United States Patent [19]

Vogelman

[11] 4,144,763
[45] Mar. 20, 1979

[54] NON-INVASIVE METHOD FOR THE MEASUREMENT OF BODY FAT

[76] Inventor: Joseph H. Vogelman, 48 Green Dr., Roslyn, N.Y. 11576

[21] Appl. No.: 891,183

[22] Filed: Mar. 29, 1978

[51] Int. Cl.² .............................................. G01N 9/02
[52] U.S. Cl. ..................................................... 73/433
[58] Field of Search ....................... 73/433, 149, 32 R

[56] References Cited

U.S. PATENT DOCUMENTS

| 2,304,731 | 12/1942 | Fairbairn | 73/32 |
| 3,455,168 | 7/1969 | Taylor et al. | 73/433 |

Primary Examiner—Anthony V. Ciarlante
Attorney, Agent, or Firm—Hopgood, Calimafde, Kalil, Blaustein & Lieberman

[57] ABSTRACT

A non-invasive method for the measurement of body fat which may be used to measure living objects. A pair of airtight chambers are used to measure the body volume which is determined by the change in pressure resulting from the presence of the body in an enclosed chamber and utilizing Boyle's law. The second chamber in which the object is to be placed may be of known or unknown volume and hence can be adjustable. The fat fraction of the body is computed from the known relationship between body density and fat.

4 Claims, 1 Drawing Figure

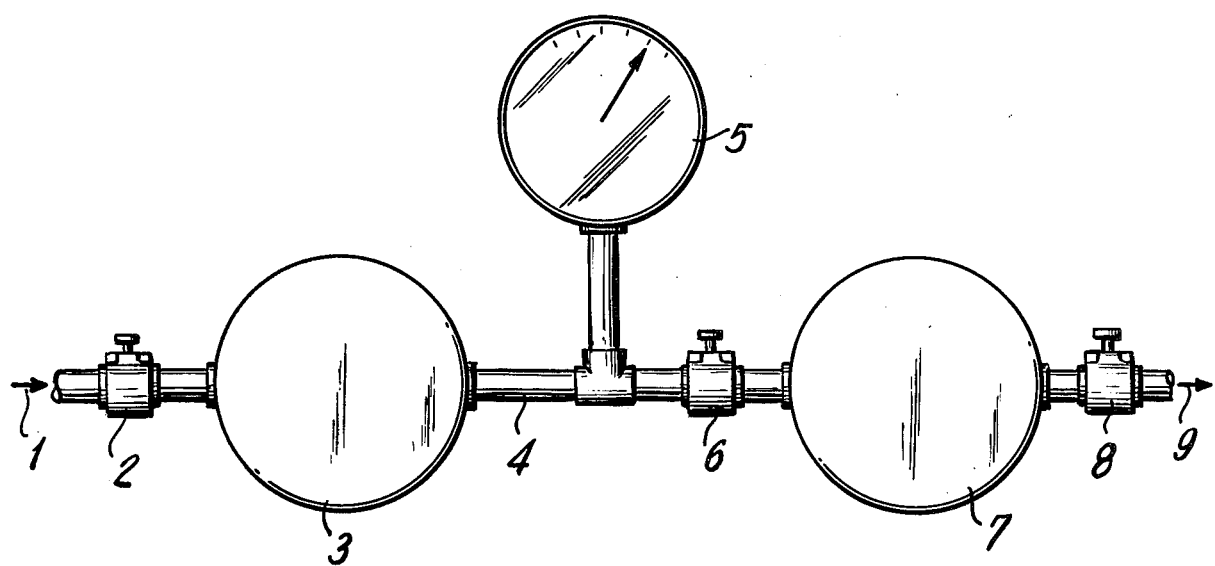

NON-INVASIVE METHOD FOR THE MEASUREMENT OF BODY FAT

BACKGROUND OF THE INVENTION

The determination of the density of an animal or a human being is an important factor in assessing the physical well-being of the individual or animal. As a result, such measurements of body density are being made with increasing frequency, not only with athletes, with whom such measurements have long been common.

Body density is determined by the combination of the protein, water, electrolytes (minerals) and fat content of the body. Since the concentrations of protein, water and electrolytes vary only slightly, the difference between the lean body and the fat body is determined by the proportion of fat to the total mass.

In the past, body density has been determined by weighing the body, and by measuring the amount of water displaced by the body and calculating the density from the weight to volume ratio. This method has proven to be inaccurate since the volume of air in the lungs and other body cavities is an unknown factor and contributes serious errors to the measured displacement volume.

Various methods and apparatus have been proposed for the measurement of the density of inanimate objects, such as that disclosed in U.S. Pat. No. 2,304,731 (Fairbairn), which discloses a method for determining the density of a bale of wool. However, such methods generally subject the object to be tested in a vacuum or a decrease in pressure. Such methods clearly can not be used to measure the density of a living body which must breathe during the measuring process.

SUMMARY OF THE INVENTION

In accordance with the invention, a non-invasive method for the measurement of body fat is provided. The method is particularly suitable for the measurement of body fat of living subjects which must respirate during the measuring process. The method consists of pressurizing a chamber above atmospheric pressure and measuring the pressure therein. The object to be measured is then placed in a second chamber, of known or unknown volume, which can be maintained at atmospheric pressure. Both chambers are then sealed from the outside environment, and then the pressure of the first chamber is routed to the second chamber and the final pressure of the two chambers is then measured. By equations developed from Boyle's law, the initial and final pressures may be used to calculate the volume of the body within the chamber. Further calculations involving empirical equations derived from known densities of the body are made to calculate the percentage of body fat in the measured object.

Accordingly, it is an object of this invention to provide an improved method for the measurement of body fat of living objects which must respirate during the measuring process.

It is a further object of this invention to provide an improved method for the measurement of body fat in which breathing of the object during the measuring process will not affect the accuracy of the results.

Another object of this invention is to provide an improved method for the measurement of body fat utilizing a specimen holding chamber which can be of any volume, known or unknown.

Still another object of this invention is to provide an improved method for the measurement of body fat utilizing a specimen chamber which may be made adjustable to fit the size requirement of the subject to be measured.

Still other objects will become apparent from a reading of the specification, when taken in conjunction with the drawing which illustrates diagramatically the apparatus used to carry out the method of the instant invention.

DESCRIPTION OF THE PREFERRED EMBODIMENTS

The drawing illustrates the apparatus used in carrying out the non-invasive method for the measurement of body fat. The apparatus consists of a first airtight chamber 3 of volume A and a second airtight chamber 7 of volume B which are inter-connected by means of conduit 4. Chamber 3 may be pressurized by means of a pump or a source of pressure (not shown) input through an orifice 1, and the pressure is maintained by closing a valve 2. Valve 2 may be either a manually controlled valve or a one-way valve permitting flow only into chamber 3. Conduit 4 inter-connecting chamber 3 with chamber 7 also includes a pressure measuring device 5 of any suitable type. A valve 6 is also located in conduit 4 between pressure measuring device 5 and chamber 7.

The method of the instant invention permits the volume of an object placed into chamber 7 to be measured even if the volume B is unknown, since this volume may be readily calculated if the volume A is known. Thus, chamber 7 may be so constructed as to be adjustable in order to accommodate various sizes of objects to be measured. The formula for determining unknown volume B of chamber 7 is derived from Boyle's gas law:

$$I_c \times A/T_0 = F_c \times (A + B)/T_1$$

Where:
$I_c$ = Initial Pressure
$A$ = Initial Volume
$T_0$ = Initial Temperature
$F_c$ = Final Pressure
$A + B$ = Final Volume
$T_1$ = Final Temperature If the temperature is allowed to stabilize before making pressure measurements, $T_0$ will equal $T_1$ and, therefore, the temperatures may be canceled from both sides of the equation, and the pressure differential alone may be used to indicate the volume of chamber B.

For example, assuming temperature stabilization, if volume A of chamber 3 is equal to volume B of chamber 4, the differential pressure (compared to the ambient pressure originally in chamber B) will be halved:

$$I_c \times A = (\tfrac{1}{2} \times I) \times (2 \times A)$$

The final volume is thus $A + B$, or twice the initial volume A.

The body to be measured is now placed into chamber 7, the free volume is equal to B minus the volume of the body (X) and repeating the above operation would result in a final pressure as follows:

$$F_c = I_c \times A/2 \times (A - X)$$

Thus, it is seen that the volume of an unknown body can be determined from the pressure differential measured by the above-described apparatus.

Since the volume B of chamber 7 may be expressed as a function of the initial volume, initial pressure and final pressure, it is unnecessary to calculate volume B if it is unknown, because the volume of the object to be measured can be calculated without knowing volume B. This calculation involves making a first calibration measurement with chamber 7 empty, and a second measurement utilizing apparently the same initial pressure with the object placed in chamber 7. The volume of the object in the chamber may then be calculated, as more particularly described below without the need for calculating volume B.

A calibration run with chamber 7 empty, and assuming temperature stabilization, gives the following relationship between the volumes of known chamber 3 and unknown chamber 7;

$$B = A (I_c/F_c - 1)$$

After the calibration run is performed, the object to be measured is placed in chamber 7 with valve 8 open so that the chamber is at atmospheric pressure. Valve 6 should be closed to segregate chamber 3 from chamber 7. Chamber 3 is then pressurized to the pressure $I_X$, which for convenience may be approximately the same as pressure $I_c$ during the calibration run. Pressure $I_X$ should be a pressure above atmospheric pressure and it may be read directly on indicating device 5. Valve 2 is then closed and valve 6 is then opened which will cause the pressures in chamber 3 and chamber 7 to equalize. The temperature should also be allowed to stabilize at which time a final pressure $F_X$ may be read on device 5.

The unknown body's volume X is then given by:

$$X = A + B - (A \times I_X/F_X)$$

Substituting the value of B in terms of A and rearranging the equation shows that the unknown volume is given by the formula:

$$X = A (I_c/F_c - I_X/F_X)$$

Thus, it is seen that once a calibration run has been performed, there is no need to separately calculate volume B and that the unknown volume is easily given by the above equation.

It can be readily seen that thermometers in chambers 3 and 7 would permit measuring unknown body volumes without temperature equalization. The operation of the apparatus may also be automated by the use of a microprocessor control unit which would automatically close valve 2 at the desired pressure, operate valves 6 and 8, and automatically compute the unknown volume, correcting for temperature variations, from the pressures on pressure indicating device 5.

The densities of the major components of a living body at a temperature 37° C. (98.6° F.) are as follows:
Fat = 0.900 gm/cc
Water = 0.993 gm/cc
Protein = 1.340 gm/cc
Mineral = 3.000 gm/cc Once the volume of the unknown object is ascertained, the density may be ascertained from a measurement of the weight of the body (density = weight/volume) and then it is a simple matter to calculate the fat fraction of the body, which is given by the formula:

$$\text{Fat Fraction} = \frac{4.201}{\text{Density (in gm/cc)}} - 3.813$$

This formula has been empirically derived from body measurements, since as previously noted, the concentration of protein, water and minerals remain fairly constant, the differential in body density depends upon the fat content of the body. The above equation provides the decimal fraction of fat content of the body. Thus, a result of 0.1 would indicate a very thin person, while a result of 0.4 would indicate an obese person.

The method of the instant invention provides an economical, simple and accurate means for determining body fat content.

Accordingly, it is seen that the objects set forth above, among those made apparent from the preceding description, are efficiently attained and, since certain changes may be made in carrying out the above method without departing from the spirit and scope of the invention, it is intended that all matter contained in the above description shall be interpreted as illustrative and not in a limiting sense.

It is also to be understood that the following claims are intended to cover all of the generic and specific features of the invention described herein and all statements of the scope of the invention which, as a matter of language, might be said to fall therebetween.

What is claimed is:

1. A method for measuring the fat of a body capable of respirating said method comprising the steps of pressurizing a first substantially airtight chamber above atmospheric pressure, measuring the pressure in said chamber, introducing said body into a substantially second airtight chamber at atmospheric pressure, sealing said second chamber from the atmosphere, communicating the pressure in said first chamber to said second chamber, measuring the resultant pressure in said first and second cahmbers, determining from the volumes and pressures of said first and second chambers the volume of said body inside said second chamber, determining the density of said body from its volume and weight, and then determining from the density of said body the fat fraction thereof.

2. The method as claimed in claim 1 wherein said fat fraction is calculated from the formula Fat Fraction = 4.201/body density − 3.813 in which said density is in gm/cc.

3. A non-invasive method for the measurement of body fat of a body capable of respirating utilizing a first airtight chamber of known volume and a second airtight chamber of unknown volume comprising the steps of pressurizing said first chamber, sealing said first chamber and measuring the initial pressure $I_c$, sealing said second chamber from the atmosphere, communicating said pressure $I_c$ from said first chamber to said second chamber, measuring the final pressure of both chambers $F_c$, returning both chambers to atmospheric pressure, sealing said first chamber from said atmospheric pressure, pressurizing said first chamber to a pressure $I_X$, placing said body to be measured within said second chamber, sealing said second chamber from atmospheric pressure, communicating the pressure of said first chamber to said second chamber, allowing the temperature of both chambers to become stabilized, measuring the final pressure $F_X$ of said chambers with said body therein determining the volume X of said body to be measured by the formula: $X = Z (I_c/F_c - I_X/F_X)$, and determining the fat fraction of said body from the volume and weight of the object and the known fat proportions of said body.

4. The method as claimed in claim 3 wherein said fat fraction is calculated from the formula Fat Fraction = 4.201/body density − 3.813 in which the density is in gm/cc.

* * * * *